US00PP25638P3

(12) United States Plant Patent
Tufaro

(10) Patent No.: US PP25,638 P3
(45) Date of Patent: Jun. 23, 2015

(54) STRAWBERRY PLANT NAMED 'MARGHERITA'

(50) Latin Name: ***Fragaria×ananassa* Duchesne**
Varietal Denomination: Margherita

(71) Applicant: Sociedad Nova Siri Genetics s.n.c. di Tufaro Nicola & C., Nova Siri (MT) (IT)

(72) Inventor: Nicola Tufaro, Nova Siri (IT)

(73) Assignee: SOCIEDAD NOVA SIRI GENETICS S.N.C., Nova Siri (MT) (IT)

( * ) Notice: Subject to any disclaimer, the term of this patent is extended or adjusted under 35 U.S.C. 154(b) by 203 days.

(21) Appl. No.: 13/987,140

(22) Filed: Jul. 3, 2013

(65) Prior Publication Data

US 2014/0020144 P1 Jan. 16, 2014

(30) Foreign Application Priority Data

Jul. 10, 2012 (QZ) ..... PBR 2012/1378

(51) Int. Cl.
*A01H 5/00* (2006.01)
*A01H 5/08* (2006.01)

(52) U.S. Cl.
USPC ..... Plt./209
CPC ..... *A01H 5/0893* (2013.01)

(58) Field of Classification Search
USPC ..... Plt./209
See application file for complete search history.

*Primary Examiner* — Annette Para
(74) *Attorney, Agent, or Firm* — Buchanan, Ingersoll & Rooney P.C.

(57) ABSTRACT

A new and distinct short-day strawberry cultivar is provided. Attractive early-ripening substantially uniform bright red conical fruit having a firm flesh is formed in good yields. White inflorescence is formed on an early basis that is disposed at approximately the same level as the foliage. A calyx commonly is displayed that is smaller than the corolla when open. A dense upright globular growth habit is displayed.

8 Drawing Sheets

Botanical/commercial classification: *Fragaria×ananassa* Duchesne/Strawberry Plant.

Varietal denomination: cv. Margherita.

BACKGROUND OF THE INVENTION

The new and distinct short-day strawberry cultivar of the present invention was the product of a controlled breeding program that was carried out at Nova Siri (MT) Italy located at 40° 08' 40" N.-16° 39' 40" E. and 10 meters above sea level. The female parent (i.e., the seed parent) was the 'Siris' cultivar (non-patented in the United States and EU No. 34843) and the male parent (i.e., pollen parent) was the 'Pajaro' cultivar (non-patented in the United States). The parentage of the new cultivar can be summarized as follows:

'Siris'×'Pajaro'.

The seeds resulting from the pollination were sown and small plants were obtained which were physically different from each other. Selective study and testing resulted in the identification of a single plant of the new cultivar.

The new cultivar initially was designated AD.09.06.

It was found that the new short-day strawberry cultivar of the present invention displays the following combination of characteristics:

(a) exhibits a dense, upright generally globose growth habit,
(b) displays on an early basis white inflorescence at approximately the same level as the foliage,
(c) commonly displays a calyx that is generally smaller than the corolla when open, and
(d) forms in abundance early-ripening substantially uniform large bright red conical fruit having a firm flesh.

The new cultivar of the present invention can be readily distinguished from previously known strawberry cultivars including the 'Sabrosa' cultivar (U.S. Plant Pat. No. 16,558) as indicated in detail hereafter.

The new cultivar possesses characteristics that commonly are sought by commercial strawberry growers. Substantially uniform firm bright red early-ripening fruit is provided in good yields. Accordingly, the new cultivar is considered to be a promising new plant introduction.

The new cultivar has been asexually reproduced by the use of stolons at Ochla, Poland located at 51° 848 N.-15° 447 E. and by in vitro tissue culture. No rooting problems were encountered. The combination of characteristics exhibited by the new plant has been found to be stable and is reliably transmitted to succeeding generations following such asexual reproduction. Accordingly, the new cultivar reproduces true-to-type manner by such asexual reproduction.

The new plant has been named 'Margherita'.

BRIEF DESCRIPTION OF THE PHOTOGRAPHS

The accompanying photographs show, as nearly true as it is reasonably possible to make the same in color illustrations of this character, typical specimens of the new cultivar as well as typical specimens of the 'Sabosa' cultivar (U.S. Plant Pat. No. 16,558) for comparative purposes. The plants had been asexually reproduced from stolons and were planted under the cover of plastic tunnels during mid-October 2012 at Nova Siri (MT), Italy.

Figure 14:
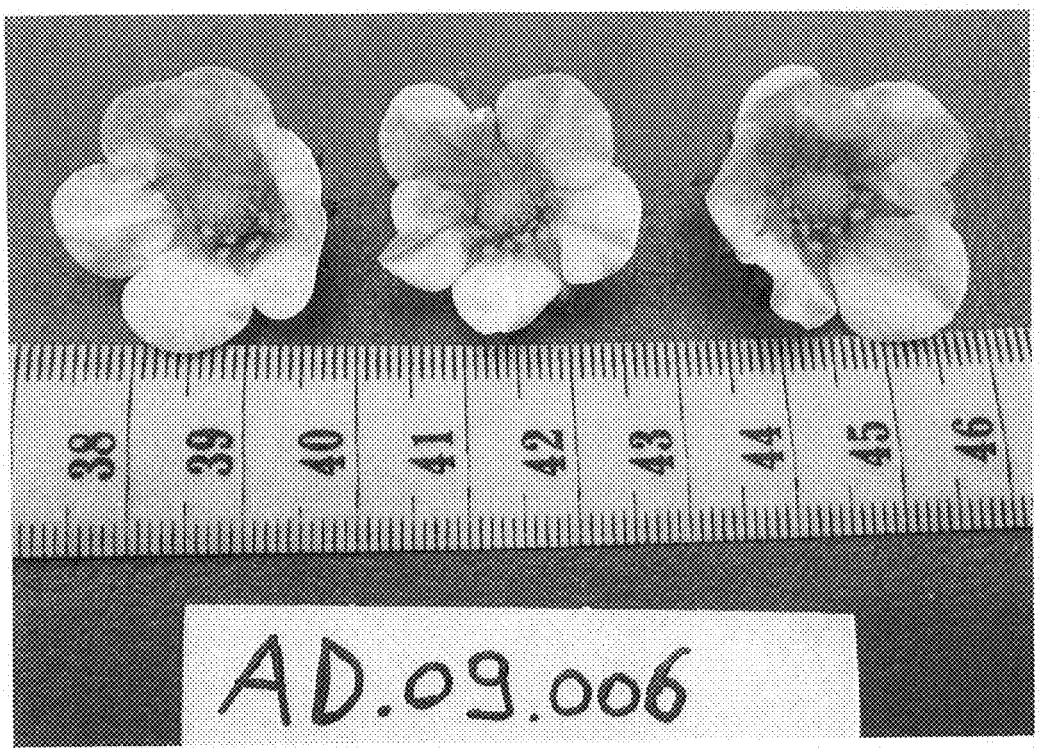

FIG. 14 illustrates an obverse view of the typical open white flowers of the new cultivar wherein the arrangement of the stamen and pistils is shown. Yellow pollen is provided in abundance. Measurement in centimeters further is included for comparative purposes.

Figure 15:
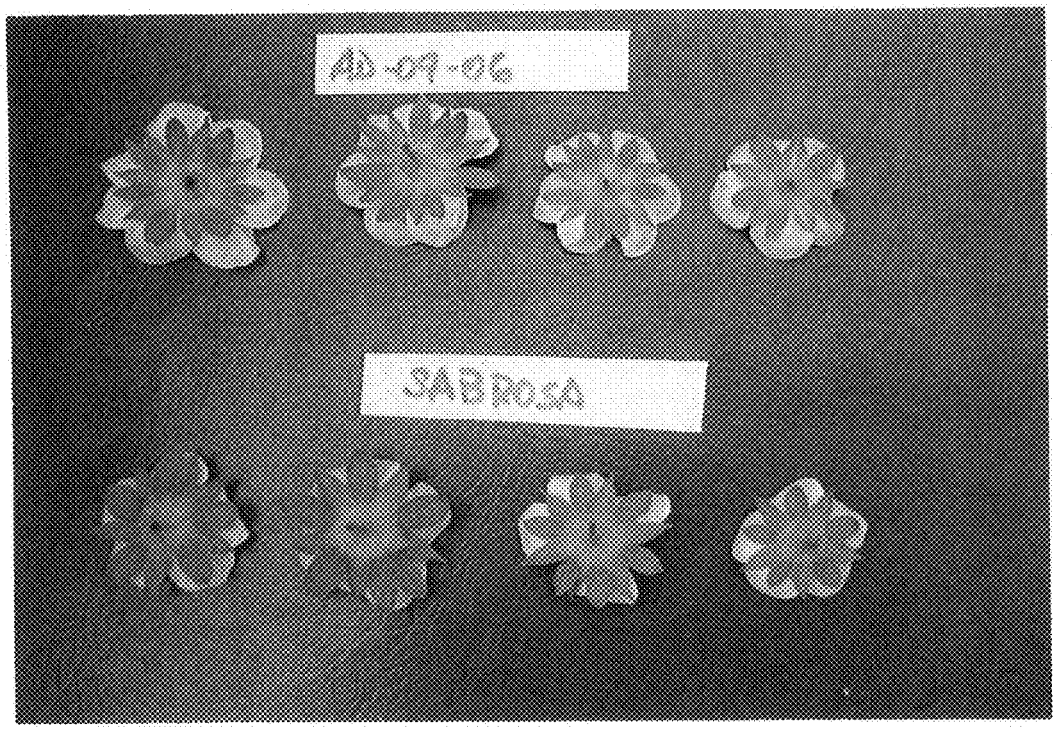

FIG. 15 illustrates for comparative purposes typical open corolla with calyx of the new 'Margherita' cultivar (top) and the 'Sabrosa' cultivar (bottom). Unlike the 'Sabrosa' cultivar, the diameter of the open calyx of the new cultivar commonly is less than that of the corolla (as illustrated).

Figure 16:
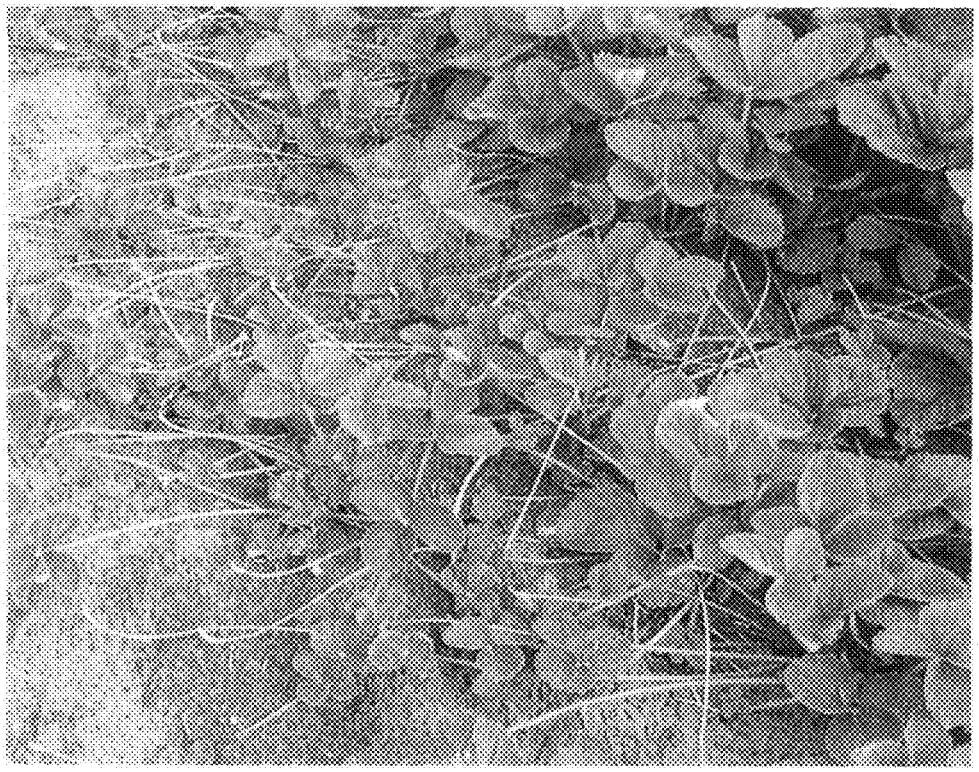

FIG. 16 illustrates typical tendency for numerous stolon formation exhibited by the new cultivar.

Figure 17:
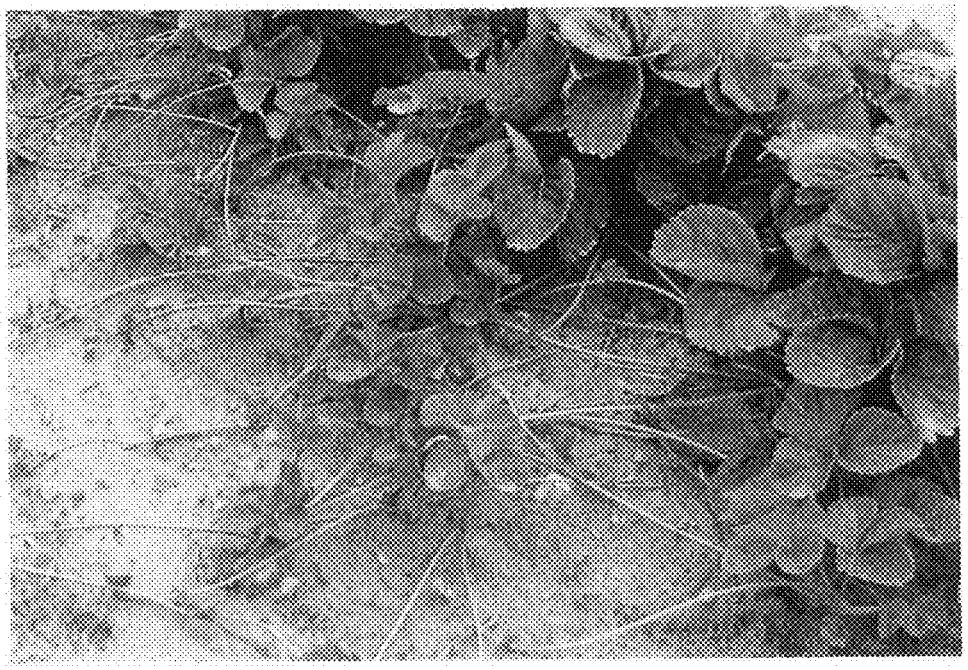

FIG. 17 illustrates for comparative purposes the typical less frequent stolon formation exhibited by the 'Sabrosa' cultivar.

DETAILED BOTANICAL DESCRIPTION

The described plants had been asexually reproduced by the use of stolons and were growing under the cover of plastic tunnels at Nova Siri (MT) Italy. The chart used in the identification of color is The R.H.S. Colour Chart (1995 Edition or equivalent) of The Royal Horticultural Society, London, England. Reference to common color terms is to be accorded ordinary dictionary significance.

Botanical class: *Fragaria×ananassa*, Duchesne, cv. 'Margherita'.

Plant:

*Type.*—Short-day.

*Configuration.*—Upright, relatively dense, and generally globose.

*Vigor.*—Medium strong.

*Height.*—Commonly approximately 25 cm on average.

*Width.*—Commonly approximately 28 on average.

*Leaflets.*—Medium in size, commonly up to approximately 9.5 cm in length on average and up to approximately 8 cm in width on average; the terminal leaflet commonly is longer in length than width and commonly is approximately 8.5 cm in length and approximately 7 cm in width, possess a concave cross section, a serrate to crenate margin, and an acute base; blistering commonly is absent; the glossiness on the upper surface is medium; and variegated coloration commonly is absent with the upper surface coloration commonly being near Green Group 141A to 141B and the under surface commonly being near Green Group 141C to 143D. Such coloration commonly is darker than that of the 'Sabrosa' cultivar.

*Stolons.*—Numerous in quantity, medium pubescence in density, commonly near Green Group 141A to 142B in coloration, and commonly bear some weak to medium anthocyanin coloration commonly near Red-Purple Group 65C to 65D. Stolons commonly are produced somewhat more numerously than the 'Sabrosa' cultivar (i.e., approximately 30 to 35% more) with anthocyanin coloration commonly being absent on the stolons of the 'Sabrosa' cultivar.

*Petioles.*—Commonly approximately 17 to 21 cm in length on average, near Green Group 149A in coloration, and commonly bear horizontally disposed fine pubescence.

Figure 12:
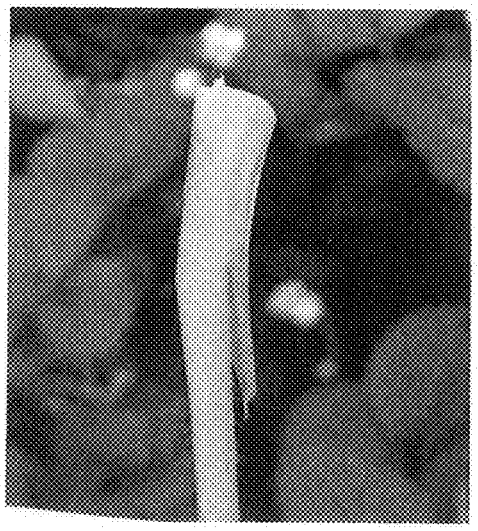
FIG. 12 illustrates a typical stipule of the new cultivar which tends to be larger than that of the 'Sabrosa' cultivar and to bear some anthocyanin coloration unlike that of the 'Sabrosa' cultivar.
Figure 13:
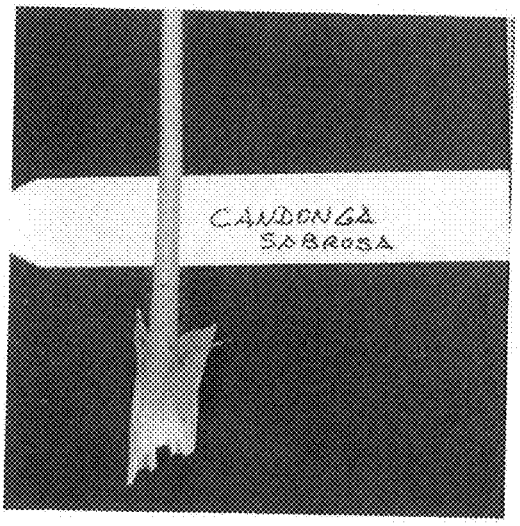
FIG. 13 illustrates for comparative purposes a typical smaller stipule of the 'Sabrosa' cultivar where anthocyanin coloration is absent.

*Stipules.*—Larger than those of the 'Sabrosa' cultivar as illustrated in FIGS. 12 and 13, and commonly bear some anthocyanin coloration unlike the stipules of the 'Sabrosa' cultivar where anthocyanin coloration was not observed.

Inflorescence:

*Flowering time.*—Early.

*Flower number.*—Medium, commonly 4 or 5.

*Pedicel hairs.*—Pubescence generally disposed upwards.

*Size.*—Large, with primary flowers commonly being approximately 2.8 cm in diameter on average, and secondary flowers commonly being approximately 2.5 cm in diameter on average.

*Petals.*—Overlapping, commonly number approximately 5 to 8 on average, commonly greater in width than length, and near White Group 155B to 155C in coloration.

*Anthers.*—Commonly number approximately 25 on average and disposed slightly above the stamens. The plant is self fertile.

*Sepals.*—Generally lanceolate in configuration, outwardly disposed, commonly number approximately 10 to 14 which can be compared to approximately 10 to 12 for the 'Sabrosa' cultivar, commonly approximately 4 to 7 mm in length on average and approximately 2 to 3 mm in width on average at the broadest point, unlike the 'Sabrosa' cultivar the diameter of the open calyx commonly is generally less than that of the corolla (as illustrated in FIG. 15), and the coloration is commonly near Yellow-Green Group 144B to 144C when viewed from below the open corolla.

Fruit:

*Bearing.*—Non-remontant.

*Timing.*—Early-fruiting commonly with approximately 30 to 35 days from first blooming to first fruit ripening. This can be compared to approximately 35 to 40 days between first blooming and first fruit ripening for the 'Sabrosa' cultivar.

*Shape.*—Generally conical in configuration, and substantially uniform with commonly only a slight shape difference between terminal and other fruit.

*Size.*—Large, with the primary fruit commonly being approximately 5 to 5.5 cm in length and width at the broadest point.

*Surface.*—Generally smooth with strong glossiness.

*External color.*—Substantially uniform and commonly near Red Group 40A to Red Group 44B.

*Internal color.*—Medium red, and commonly near Red Group 40A to 40B.

*Firmness.*—Good, with medium flesh firmness.

Figure 1:
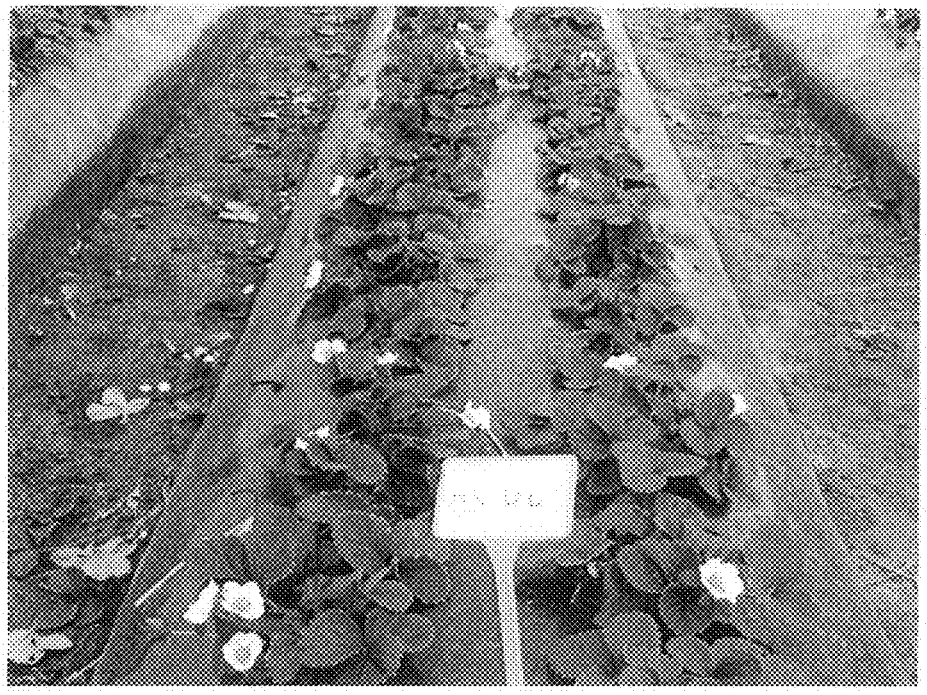
FIG. 1 shows rows of flowering young plants of the new cultivar on Jan. 15, 2013 where the flowers are disposed at approximately the same level as the foliage.
Figure 2:
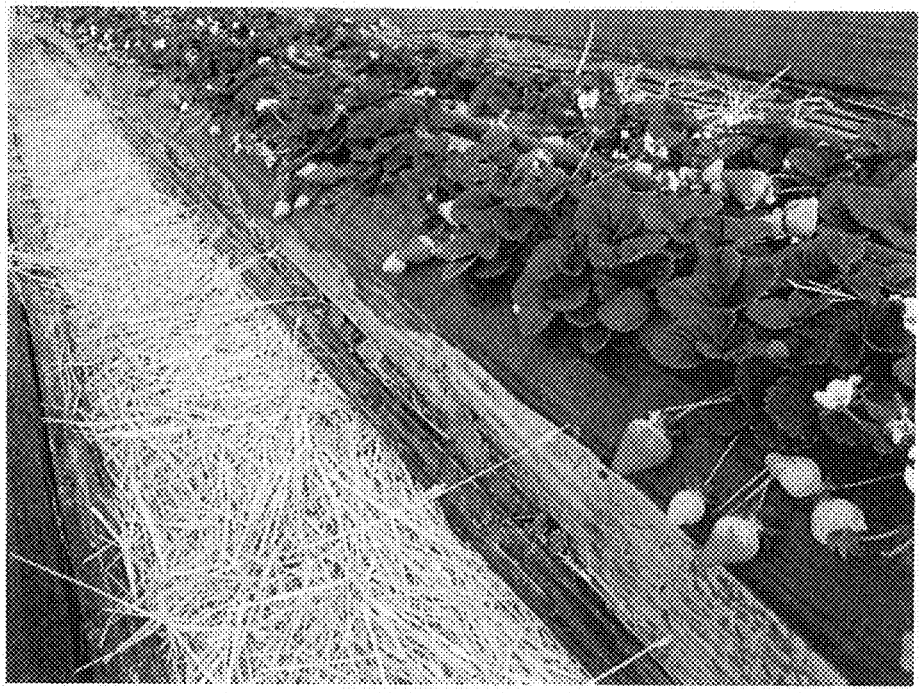
FIG. 2 shows fruiting plants of the new cultivar on Feb. 15, 2013 wherein the dense growth habit is shown.
Figure 3:
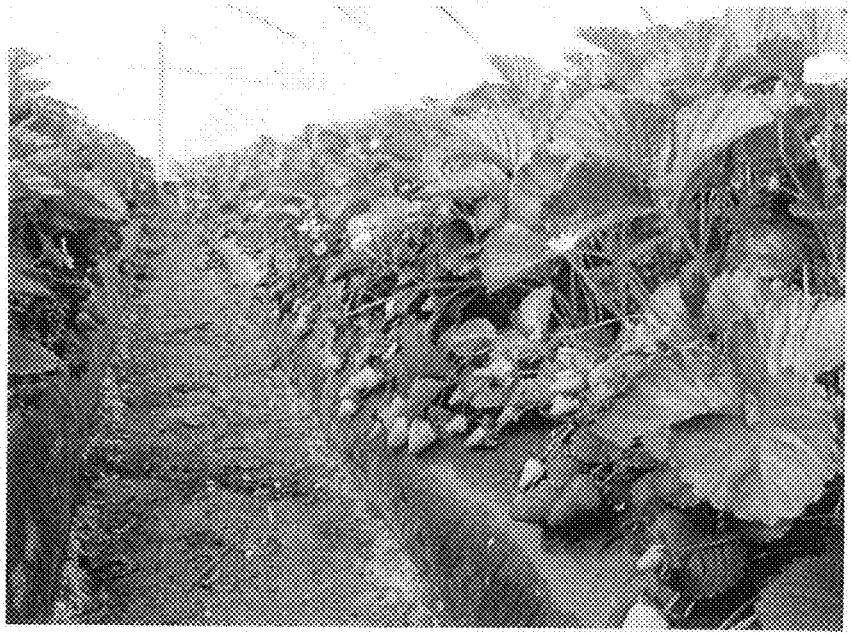
FIG. 3 shows more mature fruiting plants of the new cultivar on Apr. 15, 2013 where the plant density is further illustrated.
Figure 4:
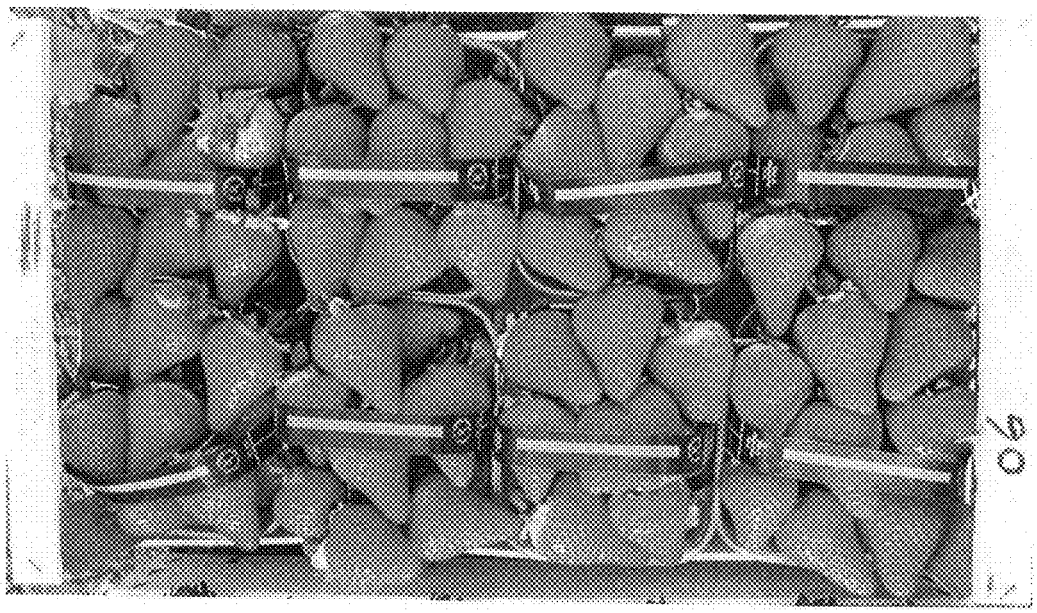
FIG. 4 shows a crate of the fruit of the new cultivar that was collected on Mar. 15, 2013. The overall substantial uniformity of fruit shape and coloration is apparent with the virtual absence of second class fruit.
Figure 5:
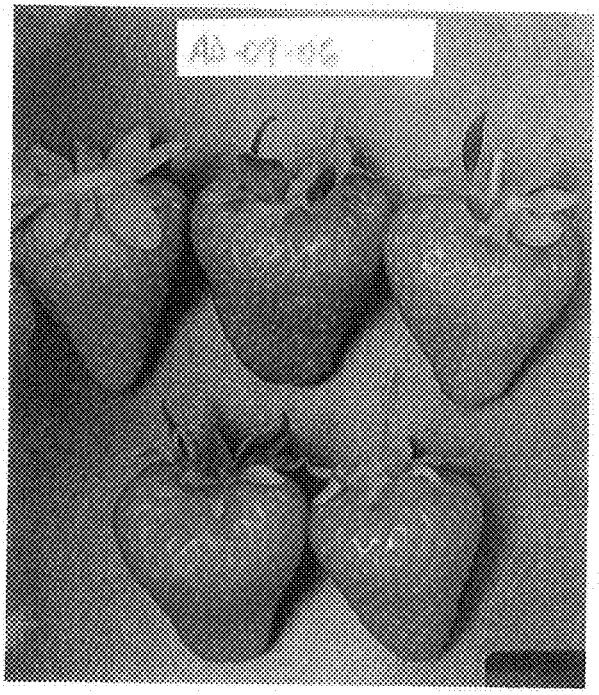
FIG. 5 shows a close view of the typical attractive conical fruit of the new cultivar. The fruit length and width at the widest point are substantially the same (i.e., near 1:1).
Figure 6:
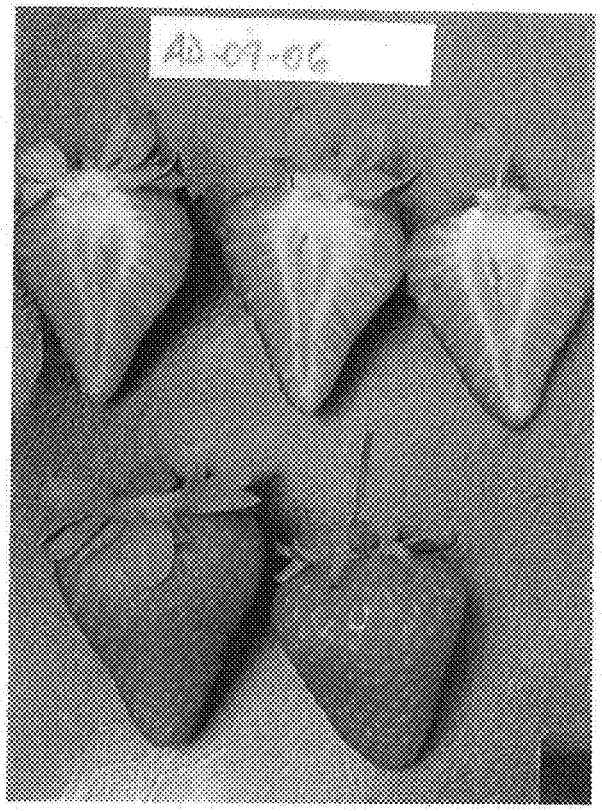
FIG. 6 shows close internal (top) and external (bottom) views of typical conical fruit of the new cultivar. The fruit cavity is small or absent.
Figure 7:
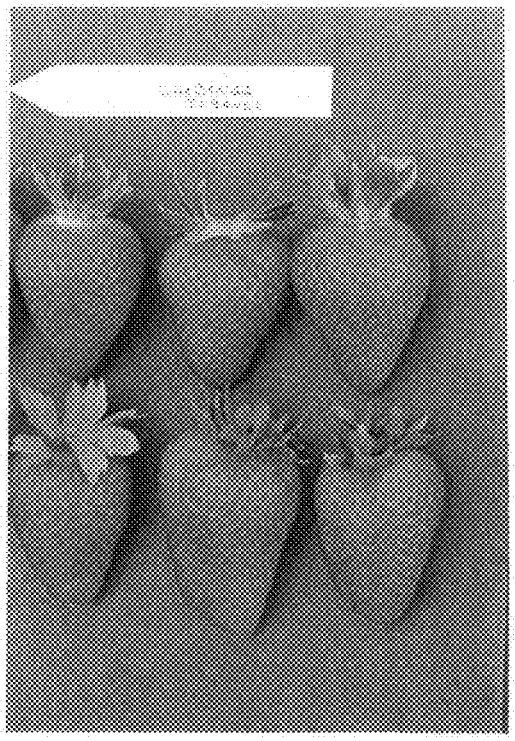
FIG. 7 shows for comparative purposes typical fruit of the 'Sabrosa' cultivar wherein the length to width ratio is approximately 1.2 to 1.3:1, unlike the near 1:1 ratio of the new cultivar.
Figure 8:
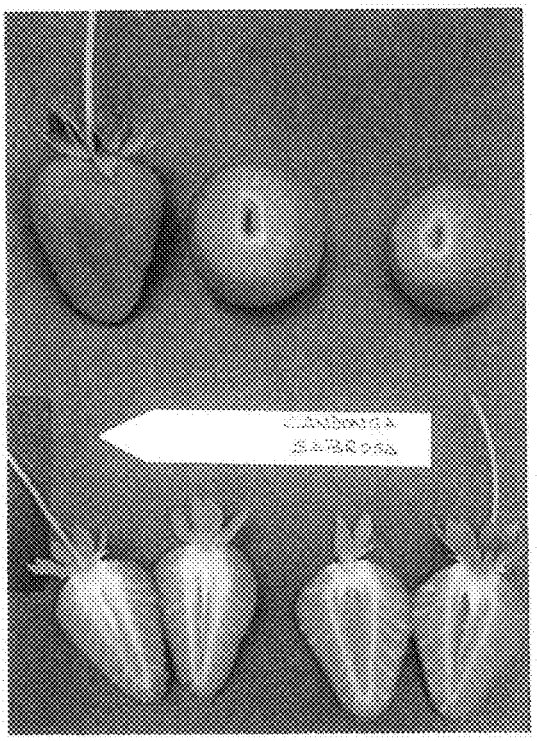
FIG. 8 shows for comparative purposes the internal nature of typical fruit of the 'Sabrosa' cultivar where a more pronounced variety is illustrated.
Figure 9:
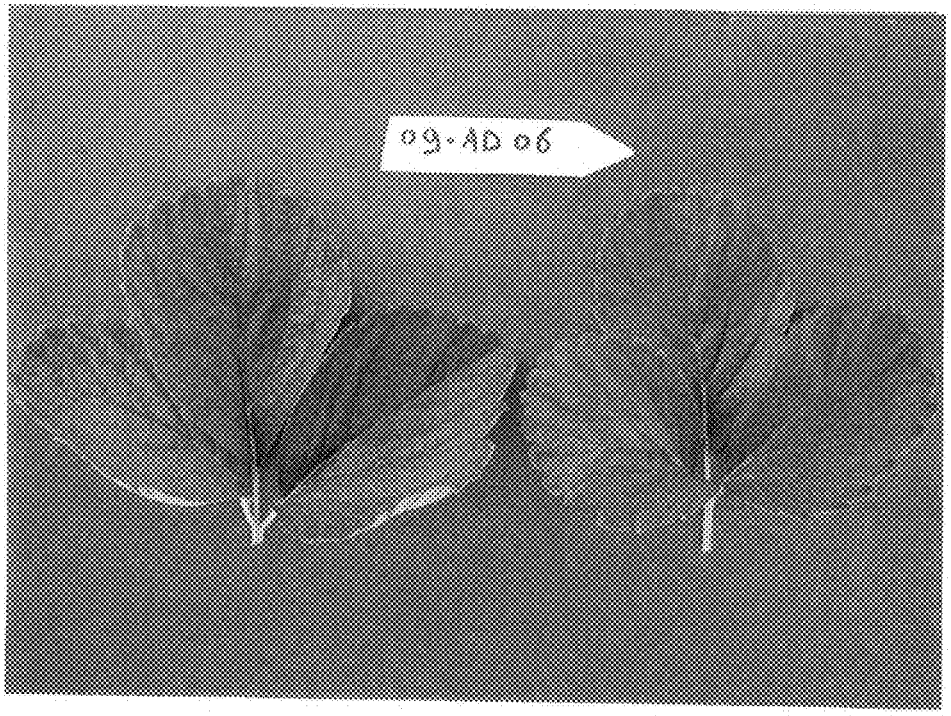
FIG. 9 shows the upper (i.e., adaxial) surfaces of a pair of typical leaves of the new cultivar. The terminal leaflet, unlike that of the 'Sabrosa' cultivar, tends to be longer than its width.
Figure 10:
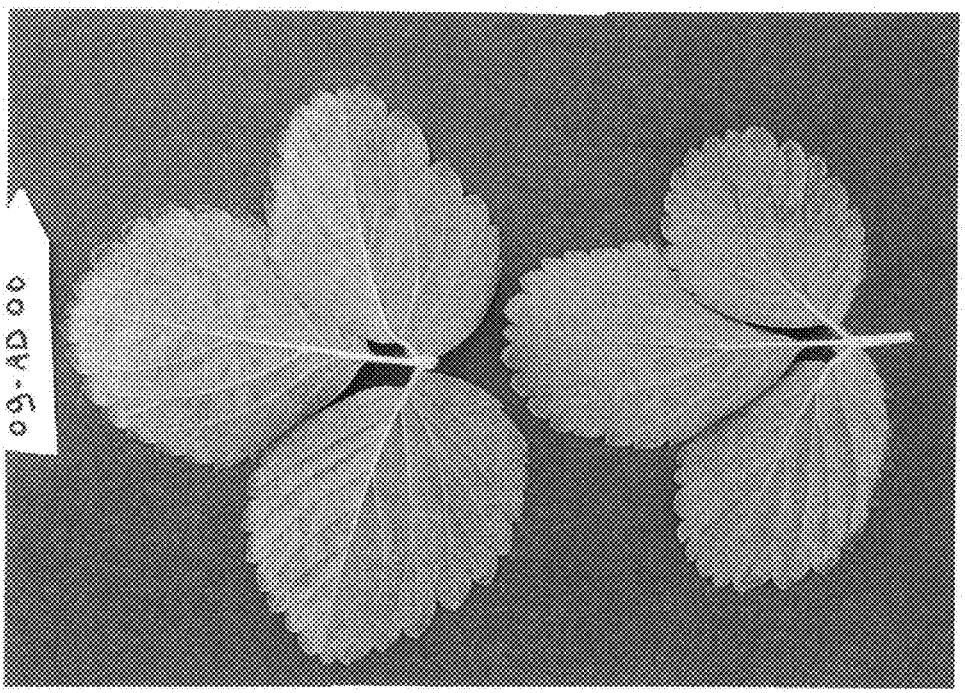
FIG. 10 shows the under (i.e., abaxial) surfaces of a pair of typical leaves of the new cultivar. The slight elongation of the terminal leaflets is similarly illustrated.
Figure 11:
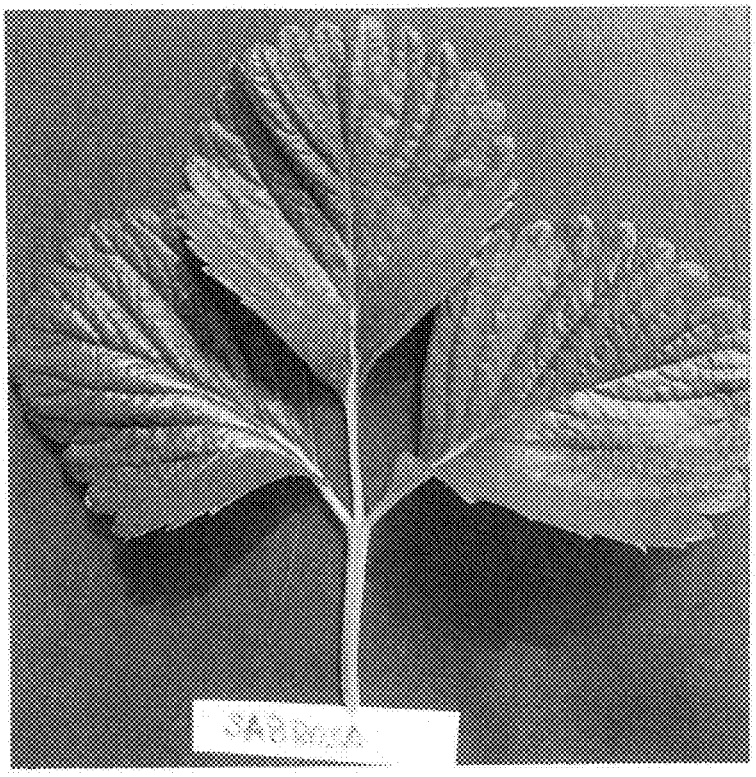
FIG. 11 shows for comparative purposes a typical leaf of the 'Sabrosa' cultivar wherein an elongation of the terminal leaflet is absent.

*Cavity.*—Very small or absent fruit cavity (as illustrated in FIG. 6).

*Achenes.*—Located below the fruit surface and cover nearly the entire fruit surface commonly with only a narrow band of 3 to 4 mm where achenes are absent, and commonly near Orange-Red Group 33B to 33C in coloration.

*Calyx.*—Commonly substantially level at end of fruit with strong adherence to fruit.

*Peduncle.*—Approximately 10 to 12 cm in length on average for primary and secondary fruit, approximately 1.5 mm in diameter on average, commonly near Yellow-Green Group 149A in coloration.

*Pedicel.*—Commonly with pubescence extending slightly outwards.

SUPPLEMENTAL COMPARATIVE DATA

Hereafter, comparative fruit data is provided for the new 'Margherita' cultivar and the 'Sabrosa' cultivar. On Oct. 15, 2012 plots of fifty (50) plants of each cultivar were planted in four (4) replications at Nova Siri (MT), Italy. The plants had been asexually reproduced by the use of stolons and were growing under the cover of plastic tunnels. The fruit was evaluated and compared during 2013 on the dates indicated. Average data is presented.

Accumulated Production of First Quality Fruit (g/plant)

| Cultivar | February 30$^{th}$ | March 30$^{th}$ | April 30$^{th}$ | May 30$^{th}$ |
|---|---|---|---|---|
| 'Margherita' | 1.65 | 124 | 528 | 883 |
| 'Sabrosa' | none | 73 | 270 | 589 |

Average Fruit Weight on Specified Dates

| | March 30$^{th}$ | | April 30$^{th}$ | | May 30$^{th}$ | |
|---|---|---|---|---|---|---|
| Cultivar | First Quality (grams) | Second Quality (grams) | First Quality (grams) | Second Quality (grams) | First Quality (grams) | Second Quality (grams) |
| 'Margherita' | 39.20 | 21.22 | 38.80 | 19.40 | 38.70 | 13.20 |
| 'Sabrosa' | 25.20 | 16.00 | 29.50 | 17.50 | 21.33 | 11.07 |

Comparison of Accumulated Fruit Production May 30$^{th}$

| Cultivar | First Quality (grams) | Second Quality (grams) | Total (grams) | Percent Second Quality |
|---|---|---|---|---|
| 'Margherita' | 883 | 82 | 965 | 8.5% |
| 'Sabrosa' | 589 | 92 | 681 | 13.5% |

Overall Comparison of Fruit Weight

| Cultivar | g/fruit |
|---|---|
| 'Margherita' | 30.45 |
| 'Sabrosa' | 22.50 |

Fruit Analysis

| | 'Margherita' | 'Sabrosa' |
|---|---|---|
| Firmness (average)* | 0.60 | 0.63 |
| Dry Matter (%)** | 7.80 | 7.50 |
| pH (to 20°) | 3.55 | 3.50 |
| Acidity as Anhydride Citric (%) | 0.75 | 0.75 |
| Soluble Solids (% Brix) | 8.27 | 8.66 |
| Maturity Index | 11.02 | 11.54 |

*Resistance to penetration measured in kilograms using a Turoni (Italy) pentrometer (20 Kg × 0.01).
**Weight of residue from the titration of the fruit after drying at 103° C. until a constant weight is achieved.

Plants of the new 'Margherita' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct short-day strawberry plant that exhibits the following combination of characteristics:

(a) exhibits a dense, upright, generally globose growth habit, (b) displays on an early basis white inflorescence at approximately the same level as the foliage, (c) commonly displays a calyx that is generally smaller than the corolla when open, and (d) forms in abundance early-ripening substantially uniform bright red conical fruit having firm flesh;

substantially as illustrated and described.

* * * * *

UNITED STATES PATENT AND TRADEMARK OFFICE

CERTIFICATE OF CORRECTION

PATENT NO. : PP25,638 P3
APPLICATION NO. : 13/987140
DATED : June 23, 2015
INVENTOR(S) : Nicola Tufaro It is certified that error appears in the above-identified patent and that said Letters Patent is hereby corrected as shown below:

On the title page item 73 Assignee: change "SOCIEDAD NOVA SIRI GENETICS S.N.C, Nova Siri (MT) (IT)" to -- NOVA SIRI GENETICS S.R.L., Nova Siri (MT) (IT) --

Signed and Sealed this
Thirteenth Day of October, 2015

Michelle K. Lee

Michelle K. Lee
*Director of the United States Patent and Trademark Office*